US008980297B2

(12) United States Patent
Ruane et al.

(10) Patent No.: US 8,980,297 B2
(45) Date of Patent: Mar. 17, 2015

(54) THERMO-MECHANICALLY CONTROLLED IMPLANTS AND METHODS OF USE

(75) Inventors: Patrick H. Ruane, San Mateo, CA (US); Cameron L. Wilson, Moss Beach, CA (US)

(73) Assignee: J.W. Medical Systems Ltd., Weihai Shandong (CN)

( * ) Notice: Subject to any disclaimer, the term of this patent is extended or adjusted under 35 U.S.C. 154(b) by 74 days.

(21) Appl. No.: 12/892,553

(22) Filed: Sep. 28, 2010

(65) Prior Publication Data

US 2011/0022148 A1 Jan. 27, 2011

Related U.S. Application Data

(63) Continuation of application No. 12/033,586, filed on Feb. 19, 2008, now abandoned.

(60) Provisional application No. 60/890,703, filed on Feb. 20, 2007.

(51) Int. Cl.

| A61F 2/00 | (2006.01) |
|---|---|
| A61F 2/06 | (2013.01) |
| A61F 2/02 | (2006.01) |
| A61K 9/22 | (2006.01) |
| A61N 5/00 | (2006.01) |
| A61F 2/82 | (2013.01) |
| A61F 2/12 | (2006.01) |

(52) U.S. Cl.
CPC ... *A61F 2/82* (2013.01); *A61F 2/12* (2013.01); *A61F 2210/0004* (2013.01); *A61F 2250/0067* (2013.01)
USPC ...... 424/423; 623/1.1; 623/11.11; 604/890.1; 250/492.1

(58) Field of Classification Search
None
See application file for complete search history.

(56) References Cited

U.S. PATENT DOCUMENTS

| 4,069,825 A | 1/1978 | Akiyama |
|---|---|---|
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |
| 4,886,062 A | 12/1989 | Wiktor |
| 4,891,225 A | 1/1990 | Langer et al. |
| 4,950,227 A | 8/1990 | Savin et al. |
| 4,988,356 A | 1/1991 | Crittenden et al. |
| 4,994,066 A | 2/1991 | Voss |
| 4,994,069 A | 2/1991 | Ritchart et al. |
| 4,994,298 A | 2/1991 | Yasuda |
| 5,013,318 A | 5/1991 | Spranza, III |
| 5,035,706 A | 7/1991 | Giantureo et al. |
| 5,040,548 A | 8/1991 | Yock |
| 5,061,273 A | 10/1991 | Yock |
| 5,064,435 A | 11/1991 | Porter |
| 5,092,877 A | 3/1992 | Pinchuk |
| 5,102,417 A | 4/1992 | Palmaz |
| 5,104,404 A | 4/1992 | Wolff |
| 5,122,154 A | 6/1992 | Rhodes |
| 5,135,535 A | 8/1992 | Kramer |
| 5,158,548 A | 10/1992 | Lau et al. |
| 5,192,297 A | 3/1993 | Hull |
| 5,195,984 A | 3/1993 | Schatz |
| 5,201,757 A | 4/1993 | Heyn et al. |
| 5,217,495 A | 6/1993 | Kaplan et al. |
| 5,219,355 A | 6/1993 | Parodi et al. |
| 5,226,913 A | 7/1993 | Pinchuk |
| 5,246,421 A | 9/1993 | Saab |
| 5,261,887 A | 11/1993 | Walker |
| 5,273,536 A | 12/1993 | Savas |

(Continued)

FOREIGN PATENT DOCUMENTS

| CN | 1856280 A | 11/2006 |
|---|---|---|
| DE | 1 953 1659 | 3/1997 |

(Continued)

OTHER PUBLICATIONS

Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39. Colombo, "The Invatec Bifurcation Stent Solution" Bifurcation Stents: Novel Solutions, TCT 2003, Washington: Sep. 15-19, 2003, 24 pages total.
Cooley et al., "Applications of Ink-Jet Printing Technology to BioMEMs and Microfluidic Systems," Proceedings, SPIE Conference on Microfluidics and BioMEMs, (Oct. 2001).
"Drug Delivery Stent With Holes Located on Neutral Axis" Research Disclosure, Kenneth Mason Publications, Hampshire, CB, No. 429, Jan. 2000, p. 13.

(Continued)

*Primary Examiner* — Scott Long
*Assistant Examiner* — Lyndsey Beckhardt
(74) *Attorney, Agent, or Firm* — Kilpatrick Townsend & Stockton LLP

(57) ABSTRACT

An implant comprises a structure that may be implanted into tissue and that has a first material property at normal body temperature. The first material property is variable at elevated temperatures above normal body temperature. The implant also has a plurality of particles dispersed in the structure that are adapted to convert incident radiation into heat energy when irradiated with electromagnetic radiation. The particles are in thermal contact with the structure such that exposure of the particles to incident radiation raises the temperature of the structure thereby changing the first material property relative to the first material property at normal body temperature.

8 Claims, 11 Drawing Sheets

(56) References Cited

U.S. PATENT DOCUMENTS

| | | |
|---|---|---|
| 5,282,823 A | 2/1994 | Schwartz et al. |
| 5,282,824 A | 2/1994 | Gianturco |
| 5,300,085 A | 4/1994 | Yock |
| 5,312,415 A | 5/1994 | Palermo |
| 5,328,469 A | 7/1994 | Coletti |
| 5,334,187 A | 8/1994 | Fischell et al. |
| 5,391,172 A | 2/1995 | Williams et al. |
| 5,421,955 A | 6/1995 | Lau et al. |
| 5,443,498 A | 8/1995 | Fontaine |
| 5,445,646 A | 8/1995 | Euteneuer et al. |
| 5,456,713 A | 10/1995 | Chuter |
| 5,458,615 A | 10/1995 | Klemm et al. |
| 5,470,315 A | 11/1995 | Adams |
| 5,478,349 A | 12/1995 | Nicholas |
| 5,484,444 A | 1/1996 | Braunschweiler et al. |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,522,882 A | 6/1996 | Gaterud et al. |
| 5,527,354 A | 6/1996 | Fontaine et al. |
| 5,531,735 A | 7/1996 | Thompson |
| 5,533,968 A | 7/1996 | Muni et al. |
| 5,534,007 A | 7/1996 | St. Germain et al. |
| 5,545,209 A | 8/1996 | Roberts et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,195 A | 1/1997 | Taheri et al. |
| 5,593,412 A | 1/1997 | Martinez et al. |
| 5,607,444 A | 3/1997 | Lam |
| 5,607,463 A | 3/1997 | Schwartz et al. |
| 5,628,755 A | 5/1997 | Heller et al. |
| 5,628,775 A | 5/1997 | Jackson et al. |
| 5,634,928 A | 6/1997 | Fischell et al. |
| 5,639,274 A | 6/1997 | Fischell et al. |
| 5,662,675 A | 9/1997 | Polanskyj Stockert et al. |
| 5,662,703 A | 9/1997 | Yurek et al. |
| 5,670,161 A | 9/1997 | Healy et al. |
| 5,676,654 A | 10/1997 | Ellis et al. |
| 5,683,451 A | 11/1997 | Lenker et al. |
| 5,690,644 A | 11/1997 | Yurek et al. |
| 5,693,085 A | 12/1997 | Buirge et al. |
| 5,697,948 A | 12/1997 | Marin et al. |
| 5,697,971 A | 12/1997 | Fischell et al. |
| 5,702,418 A | 12/1997 | Ravenscroft |
| 5,702,419 A | 12/1997 | Berry et al. |
| 5,709,701 A | 1/1998 | Parodi |
| 5,716,393 A | 2/1998 | Lindenberg et al. |
| 5,722,669 A | 3/1998 | Shimizu et al. |
| 5,723,003 A | 3/1998 | Winston et al. |
| 5,735,869 A | 4/1998 | Fernandez-Aceytuno |
| 5,741,323 A | 4/1998 | Pathak et al. |
| 5,749,848 A | 5/1998 | Jang et al. |
| 5,749,890 A | 5/1998 | Shaknovich |
| 5,749,921 A | 5/1998 | Lenker et al. |
| 5,755,697 A | 5/1998 | Jones et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,792,144 A | 8/1998 | Fischell et al. |
| 5,797,951 A | 8/1998 | Mueller et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,090 A | 12/1998 | Schuetz |
| 5,843,092 A | 12/1998 | Heller et al. |
| 5,855,563 A | 1/1999 | Kaplan et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,899,935 A | 5/1999 | Ding |
| 5,902,332 A | 5/1999 | Schatz |
| 5,919,175 A | 7/1999 | Sirhan |
| 5,921,971 A | 7/1999 | Agro et al. |
| 5,922,020 A | 7/1999 | Klein et al. |
| 5,941,869 A | 8/1999 | Patterson et al. |
| 5,951,585 A | 9/1999 | Cathcart et al. |
| 5,961,536 A | 10/1999 | Mickley et al. |
| 5,965,879 A | 10/1999 | Leviton |
| 5,968,069 A | 10/1999 | Dusbabek et al. |
| 5,972,027 A | 10/1999 | Johnson |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik et al. |
| 5,984,957 A | 11/1999 | Laptewicz, Jr. et al. |
| 5,989,280 A | 11/1999 | Euteneuer et al. |
| 5,993,484 A | 11/1999 | Shmulewitz |
| 5,997,563 A | 12/1999 | Kretzers et al. |
| 6,004,328 A | 12/1999 | Solar |
| 6,007,517 A | 12/1999 | Anderson |
| 6,010,530 A | 1/2000 | Goicoechea |
| 6,022,359 A | 2/2000 | Frantzen |
| 6,022,374 A | 2/2000 | Imran |
| 6,027,519 A | 2/2000 | Stanford |
| 6,033,434 A | 3/2000 | Borghi |
| 6,036,725 A | 3/2000 | Avellanet |
| 6,039,721 A | 3/2000 | Johnson et al. |
| 6,042,589 A | 3/2000 | Marianne |
| 6,050,999 A | 4/2000 | Paraschac et al. |
| 6,056,722 A | 5/2000 | Jayaraman |
| 6,063,111 A | 5/2000 | Hieshima et al. |
| 6,066,155 A | 5/2000 | Amann et al. |
| 6,068,655 A | 5/2000 | Seguin et al. |
| 6,070,589 A | 6/2000 | Keith et al. |
| 6,090,063 A | 7/2000 | Makower et al. |
| 6,090,136 A | 7/2000 | McDonald et al. |
| 6,102,942 A | 8/2000 | Ahari |
| 6,106,530 A | 8/2000 | Harada |
| RE36,857 E | 9/2000 | Euteneuer et al. |
| 6,120,477 A | 9/2000 | Campbell et al. |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A | 10/2000 | Kugler |
| 6,132,460 A | 10/2000 | Thompson |
| 6,139,572 A | 10/2000 | Campbell et al. |
| 6,143,016 A | 11/2000 | Bleam et al. |
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duering |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |

(56) References Cited

U.S. PATENT DOCUMENTS

| | | |
|---|---|---|
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 | 5/2002 | Solar et al. |
| 6,409,753 B1 | 6/2002 | Brown et al. |
| 6,415,696 B1 | 7/2002 | Erickeson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,565,599 B1 | 5/2003 | Hong et al. |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B1 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,913,619 B2 | 7/2005 | Brown et al. |
| 6,918,928 B2 | 7/2005 | Wolinsky et al. |
| 6,939,376 B2 | 9/2005 | Shulz et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,004,964 B2 | 2/2006 | Thompson et al. |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,351,255 B2 | 4/2008 | Andreas |

(56) References Cited

U.S. PATENT DOCUMENTS

| | | |
|---|---|---|
| 7,402,168 B2 | 7/2008 | Sanderson et al. |
| 7,534,449 B2 | 5/2009 | Saltzman et al. |
| 7,699,886 B2 | 4/2010 | Sugimoto |
| 7,824,439 B2 | 11/2010 | Toyokawa |
| 7,892,273 B2 | 2/2011 | George et al. |
| 7,892,274 B2 | 2/2011 | Will et al. |
| 7,905,913 B2 | 3/2011 | Chew et al. |
| 7,918,881 B2 | 4/2011 | Andreas et al. |
| 7,938,851 B2 | 5/2011 | Olson et al. |
| 7,938,852 B2 | 5/2011 | Andreas et al. |
| 7,993,388 B2 | 8/2011 | Lee et al. |
| 8,016,870 B2 | 9/2011 | Chew et al. |
| 8,070,789 B2 | 12/2011 | Will et al. |
| 8,070,794 B2 | 12/2011 | Issenmann |
| 8,157,851 B2 | 4/2012 | Andreas |
| 8,257,427 B2 | 9/2012 | Andersen et al. |
| 8,282,680 B2 | 10/2012 | Kao et al. |
| 8,317,850 B2 | 11/2012 | Kusleika |
| 8,317,859 B2 | 11/2012 | Snow et al. |
| 8,486,132 B2 | 7/2013 | Snow et al. |
| 8,702,781 B2 | 4/2014 | Acosta et al. |
| 8,740,968 B2 | 6/2014 | Kao et al. |
| 2001/0001824 A1 | 5/2001 | Wu |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2001/0049549 A1 | 12/2001 | Boylan et al. |
| 2002/0007212 A1 | 1/2002 | Brown et al. |
| 2002/0032457 A1 | 3/2002 | Sirhan et al. |
| 2002/0035395 A1 | 3/2002 | Sugimoto |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0123792 A1 | 9/2002 | Burgermeister |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0013266 A1 | 1/2003 | Fukuda et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0105511 A1 | 6/2003 | Welsh et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0087965 A1 | 5/2004 | Levine et al. |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0093077 A1 | 5/2004 | White et al. |
| 2004/0098081 A1 | 5/2004 | Landreville et al. |
| 2004/0106979 A1 | 6/2004 | Goicoechea |
| 2004/0111145 A1 | 6/2004 | Serino et al. |
| 2004/0117008 A1 | 6/2004 | Wnendt et al. |
| 2004/0138737 A1 | 7/2004 | Davidson et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas et al. |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249435 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0055077 A1 | 3/2005 | Marco et al. |
| 2005/0075716 A1 | 4/2005 | Yan |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0101624 A1 | 5/2005 | Betts et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0133164 A1 | 6/2005 | Fischer et al. |
| 2005/0137622 A1 | 6/2005 | Griffin |
| 2005/0143827 A1 | 6/2005 | Globerman et al. |
| 2005/0149159 A1 | 7/2005 | Andreas et al. |
| 2005/0149168 A1 | 7/2005 | Gregorich |
| 2005/0165378 A1 | 7/2005 | Heinrich et al. |
| 2005/0171568 A1 | 8/2005 | Duffy |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1* | 9/2005 | Gale et al. ............... 623/1.15 |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288763 A1 | 12/2005 | Andreas et al. |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0177476 A1 | 8/2006 | Saffran |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |

(56) References Cited

U.S. PATENT DOCUMENTS

| | | |
|---|---|---|
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |
| 2007/0292518 A1 | 12/2007 | Ludwig |
| 2008/0004690 A1 | 1/2008 | Robaina |
| 2008/0046067 A1 | 2/2008 | Toyokawa |
| 2008/0071345 A1 | 3/2008 | Hammersmark et al. |
| 2008/0077229 A1 | 3/2008 | Andreas et al. |
| 2008/0091257 A1 | 4/2008 | Andreas et al. |
| 2008/0097299 A1 | 4/2008 | Andreas et al. |
| 2008/0097574 A1 | 4/2008 | Andreas et al. |
| 2008/0125850 A1 | 5/2008 | Andreas et al. |
| 2008/0132989 A1 | 6/2008 | Snow et al. |
| 2008/0147162 A1 | 6/2008 | Andreas et al. |
| 2008/0177369 A1 | 7/2008 | Will et al. |
| 2008/0199510 A1 | 8/2008 | Ruane et al. |
| 2008/0208311 A1 | 8/2008 | Kao et al. |
| 2008/0208318 A1 | 8/2008 | Kao et al. |
| 2008/0234795 A1 | 9/2008 | Snow et al. |
| 2008/0234798 A1 | 9/2008 | Chew et al. |
| 2008/0234799 A1 | 9/2008 | Acosta et al. |
| 2008/0243225 A1 | 10/2008 | Satasiya et al. |
| 2008/0249607 A1 | 10/2008 | Webster et al. |
| 2008/0269865 A1 | 10/2008 | Snow et al. |
| 2009/0076584 A1 | 3/2009 | Mao et al. |
| 2009/0088832 A1 | 4/2009 | Chew et al. |
| 2009/0105686 A1 | 4/2009 | Snow et al. |
| 2009/0149863 A1 | 6/2009 | Andreas et al. |
| 2009/0228088 A1 | 9/2009 | Lowe et al. |
| 2009/0234428 A1 | 9/2009 | Snow et al. |
| 2009/0248137 A1 | 10/2009 | Andersen et al. |
| 2009/0248140 A1 | 10/2009 | Gerberding |
| 2009/0264979 A1 | 10/2009 | Kao et al. |
| 2009/0276030 A1 | 11/2009 | Kusleika |
| 2010/0004729 A1 | 1/2010 | Chew et al. |
| 2011/0093056 A1 | 4/2011 | Kaplan et al. |
| 2011/0125248 A1 | 5/2011 | George et al. |
| 2011/0152996 A1 | 6/2011 | Snow et al. |
| 2013/0060321 A1 | 3/2013 | Kao et al. |
| 2013/0211494 A1 | 8/2013 | Snow et al. |
| 2014/0018899 A1 | 1/2014 | Snow et al. |

FOREIGN PATENT DOCUMENTS

| | | |
|---|---|---|
| DE | 1 963 0469 | 1/1998 |
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 596 145 | 5/1994 |
| EP | 0 696 447 A2 | 2/1996 |
| EP | 0 714 640 | 6/1996 |
| EP | 0 797 963 A2 | 10/1997 |
| EP | 0 947 180 | 10/1999 |
| EP | 1 254 644 A1 | 11/2002 |
| EP | 1 258 230 | 11/2002 |
| EP | 1 266 638 B1 | 12/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1 743 603 A2 | 1/2007 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2001-190687 | 7/2001 |
| JP | 2002-538932 T | 11/2002 |
| JP | 2004-121343 A | 4/2004 |
| WO | 94/27667 A1 | 12/1994 |
| WO | WO 95/26695 A2 | 10/1995 |
| WO | 95/29647 A2 | 11/1995 |
| WO | 96/26689 | 9/1996 |
| WO | 96/33677 | 10/1996 |
| WO | 96/37167 A1 | 11/1996 |
| WO | WO 96/39077 | 12/1996 |
| WO | 97/10778 | 3/1997 |
| WO | 97/46174 | 12/1997 |
| WO | 97/48351 | 12/1997 |
| WO | 98/20810 | 5/1998 |
| WO | 98/37833 | 9/1998 |
| WO | 98/58600 | 12/1998 |
| WO | WO 99/01087 | 1/1999 |
| WO | 99/65421 | 12/1999 |
| WO | WO 00/12832 A3 | 3/2000 |
| WO | WO 00/15151 A1 | 3/2000 |
| WO | 00/25841 | 5/2000 |
| WO | 00/32136 | 6/2000 |
| WO | 00/41649 | 7/2000 |
| WO | 00/50116 | 8/2000 |
| WO | 00/51525 A1 | 9/2000 |
| WO | WO 00/56237 | 9/2000 |
| WO | 00/62708 | 10/2000 |
| WO | 00/72780 | 12/2000 |
| WO | 01/26707 | 4/2001 |
| WO | 01/34063 | 5/2001 |
| WO | 01/70297 | 9/2001 |
| WO | WO 01/91918 | 12/2001 |
| WO | 02/060344 | 8/2002 |
| WO | 02/071975 | 9/2002 |
| WO | WO 02/085253 | 10/2002 |
| WO | WO 02/098326 | 12/2002 |
| WO | 03/022178 A1 | 3/2003 |
| WO | 03/047651 | 6/2003 |
| WO | 03/051425 | 6/2003 |
| WO | 03/075797 | 9/2003 |
| WO | 2004/017865 | 3/2004 |
| WO | 2004/043301 | 5/2004 |
| WO | 2004/043510 | 5/2004 |
| WO | WO 2004/043299 A1 | 5/2004 |
| WO | WO 2004/052237 A2 | 6/2004 |
| WO | 2004/087006 | 10/2004 |
| WO | 2004/091441 | 10/2004 |
| WO | 2005/013853 | 2/2005 |
| WO | WO 2005/009295 | 2/2005 |
| WO | 2005/023153 | 3/2005 |
| WO | 2006/036939 | 4/2006 |
| WO | 2006/047520 | 5/2006 |
| WO | 2007/035805 | 3/2007 |

(56) References Cited

FOREIGN PATENT DOCUMENTS

| WO | WO 2007/053187 | 5/2007 |
|---|---|---|
| WO | 2007/146411 | 12/2007 |
| WO | 2008/005111 | 1/2008 |

OTHER PUBLICATIONS

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," J Control Release. Sep. 19, 2003;92(1-2):83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., "Parallel Production of Oligonucleotide Arrays Using Membranes and Reagent Jet Printing," BioTechniques 25:886-890 (Nov. 1998).

Tilley, "Biolimus A9-Eluting Stent Shows Promise," Medscape Medical News, Oct. 5, 2004; retrieved from the internet: <http://www.medscape.com/viewarticle/490621>, 2 pages total.

Weir et al., "Degradation of poly-L-lactide. Part 2: increased temperature accelerated degradation," Proc Inst Mech Eng H. 2004;218(5):321-30.

International Search Report and Written Opinion of PCT Application No. PCT/US2008/054437, mailed May 23, 2005; 13 pages total.

Supplementary European Search Report of EP Patent Application No. 05727731.1, dated Mar. 25, 2008, 2 pages total.

Supplementary European Search Report of EP Patent Application No. 05744136, dated Mar. 26, 2008, 3 pages total.

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

Supplementary European Search Report of EP Patent Application No. 07758831, dated Dec. 14, 2009.

International Search Report and Written Opinion of PCT Application No. PCT/US2008/061041, mailed Nov. 7, 2008, 13 pages total.

Intellectual Property Office of the Republic of China, First Office Action date of dispatch Oct. 26, 2011, 11 pages.

The State Intellectual Property Office of the People's Republic of China, Second Office Action date of dispatch Jul. 25, 2012, 23 pages.

Dongkyu Kim et al., Antibiofouling Polymer-Coated Gold Nanoparticles as a Contrast Agent for in Vivo X-ray Computed Tomography Imaging, J. Am. Chem. Soc. 2007, 129, 7661-7665, 5 pages.

Supplementary European Search Report of EP Patent Application No. 02804509, dated Dec. 13, 2006, 2 pages total.

Supplementary European Search Report of EP Patent Application No. 04749567, dated Sep. 11, 2006, 2 pages total.

International Search Report and Written Opinion of PCT Application No. PCT/US2007/086864, mailed May 13, 2008, 13 pages total.

Office Action of Japanese Patent Application No. 2006-547139, mailed Jun. 15, 2010, 5 pages total. (English translation included).

The State Intellectual Property Office of the People's Republic of China, 200880100150.2, Third Office Action date of dispatch Apr. 12, 2013, 26 pages.

\* cited by examiner

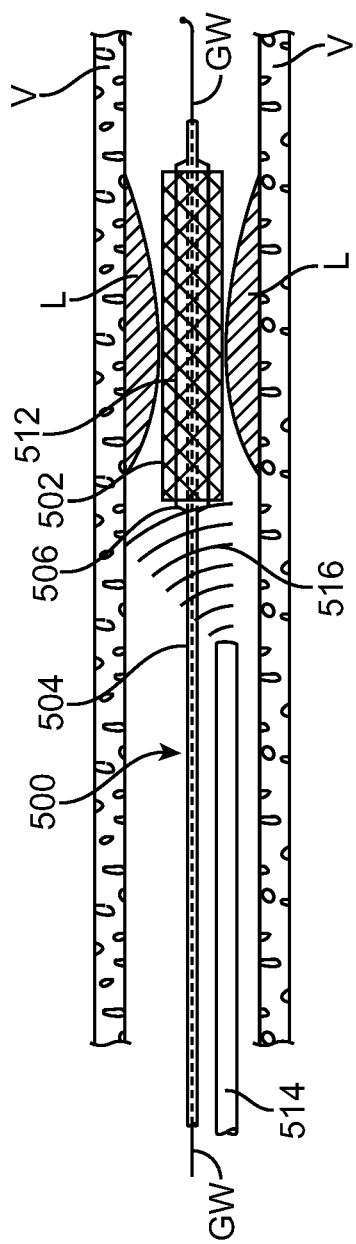
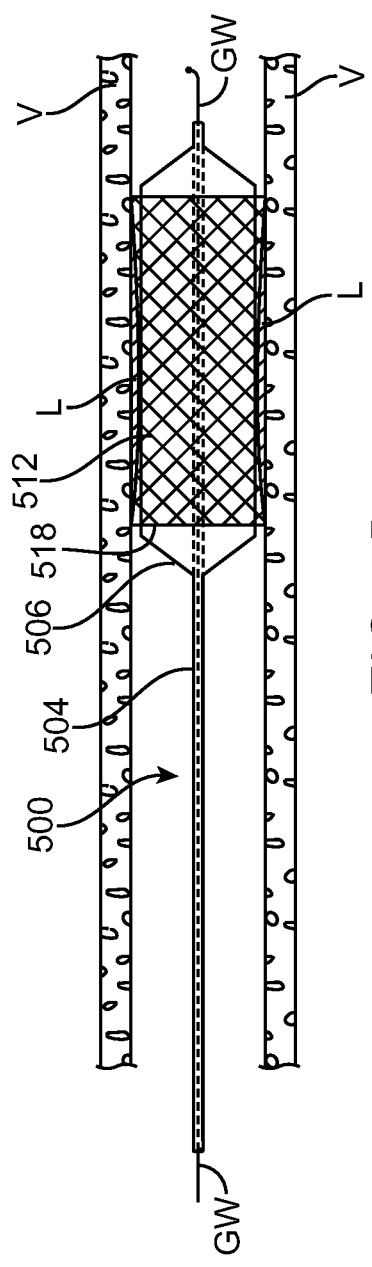

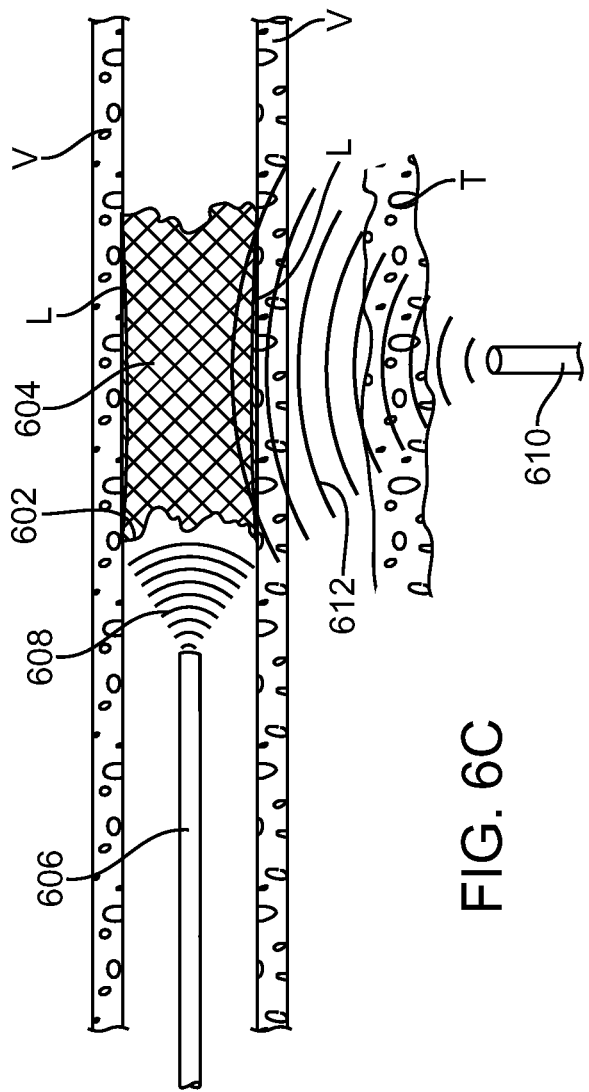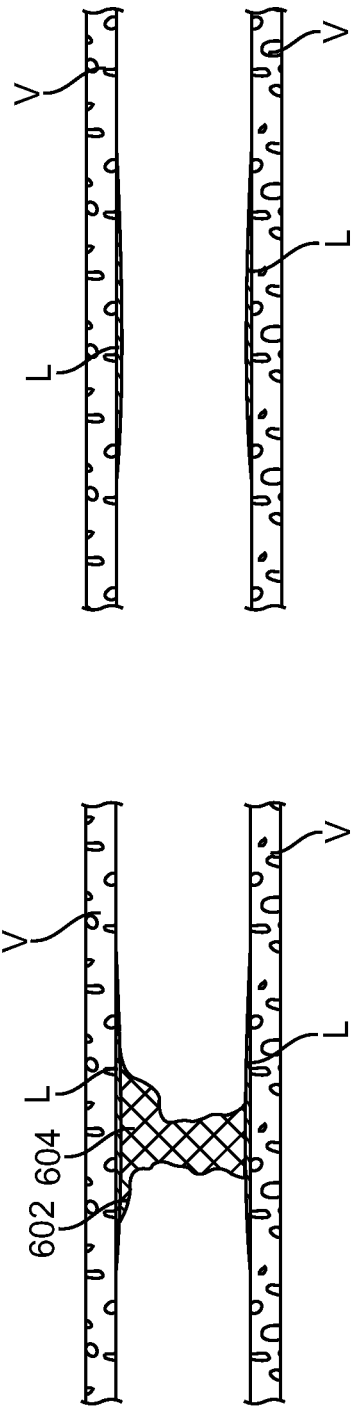

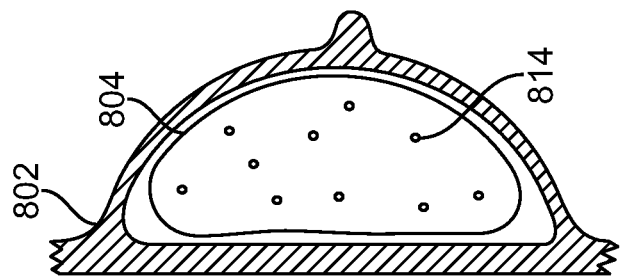
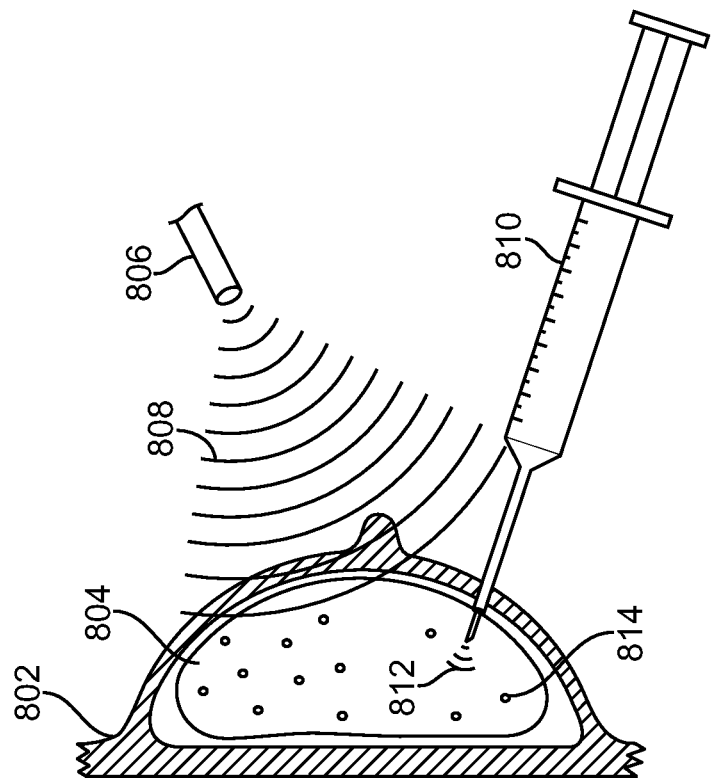
FIG. 8D
FIG. 8C

THERMO-MECHANICALLY CONTROLLED IMPLANTS AND METHODS OF USE

CROSS-REFERENCES TO RELATED APPLICATIONS

This application is a continuation of U.S. patent application Ser. No. 12/033,586, filed Feb. 19, 2008, which claims the benefit of U.S. Provisional Application No. 60/890,703, filed Feb. 20, 2007, the full disclosures of which are incorporated herein by reference.

BACKGROUND OF THE INVENTION

1. Field of the Invention

This invention relates generally to medical apparatus and methods, and more specifically to implants and biodegradable implants for use in the vascular system as well as other body lumens and cavities.

The use of implants in body tissue is becoming increasingly important in medical treatment. Examples of implant usage include alteration of tissue in cosmetic or reconstructive procedures such as breast augmentation as well as creation, preservation or closure of lumens, channels or fluid reservoirs (e.g. stenting stenotic lesions, exclusion of aneurysms or embolic coils). Implants are also used as matrices for tissue growth (e.g. orthopedic bone fusion procedures), to control unwanted tissue growth and for delivery of therapeutic agents to tissue. Implants may also be employed to join tissue surfaces together or for isolating or protecting tissue lesions in order to enable or mediate healing. Implants are also used to mediate the rate of substances or energy passing into, out of, or through tissue.

Often, implants are fabricated using various metals and/or polymers. Examples of common metals include stainless steel, titanium, nickel-titanium alloys like Nitinol and polymers such as PTFE (e.g. Teflon®), polyethylene, polyurethane and polyester are often used in implants. A potential disadvantage of these permanent implants is that the implant materials may be harder and stiffer than the surrounding tissues, thus anatomical or physiological mismatch may occur, potentially resulting in tissue damage or causing unwanted biological responses. Some materials may fatigue over time and break which can disrupt the layer of endothelial cells potentially causing thrombosis. Additionally, a permanent implant is not always required. An implant may only be required for a limited time period, therefore the implant often must be surgically explanted when it is no longer needed. To overcome some of these challenges, the use of biodegradable polymeric implants has been proposed. Examples of implantable biodegradable polymers include the aliphatic polyester polylactic acid or polylactide (PLA) and polyglycolide (PGA). PGA was originally proposed for use in suture material in the late 1960's. By the early 1970's PLA was proposed as a suture material including both the optically active poly-L-lactide (PLLA) and the racemic mixture poly-DL-lactide (PDLA). PLLA has also been used in biodegradable stents, as reported by Igaki and Tamai. A co-polymer of PLA and PGA, known as PLGA has also been proposed for use in implants. Another material which has recently been proposed (in the 1980's) for use in sutures and orthopedic implants is polydioxanone. In the mid-1990's implantable drug delivery systems using polyanhydrides were proposed by Langer et al. at the Massachusetts Institute of Technology, and more recently tyrosine derived polyarylate has seen use in hernia repair and companies are developing biodegradable stents composed of materials such as a tyrosine derived polycarbonate, poly(DTE carbonate).

While these newer biodegradable implant materials have overcome some of the challenges of earlier implant materials, other potential drawbacks still exist. For example, it is often desirable to adjust the shape of some implants in situ so that the implant conforms more accurately to the anatomy of the treatment site. However, the biodegradable polymers cannot be plastically deformed, molded or shaped at normal body temperatures since they must be solid at body temperature. The implant must therefore be heated above its glass transition temperature, $T_g$. Often the glass transition temperature is fairly high, for example PDLLA and PLLA have a $T_g$ approximately 50°-80° C., therefore in situ heating may result in localized tissue damage, thrombosis or patient discomfort. It is well known that adding an impurity to a material will change some of the material's properties such as increasing its boiling point and reducing its freezing point. Therefore, additives may be mixed with the biodegradable polymers to decrease the glass transition temperature, for example 2-10% ε-caprolactone added to 90-98% PLLA can reduce the glass transition temperature down to about 38°-55° C., but a heat source hotter than the glass transition temperature may still be required due to heat transfer inefficiencies or non-uniform heating, therefore, similar complications may still arise.

One proposed solution to the challenge of non-uniform heating is to coat the implant with a radiation absorbing material which converts radiation to heat. Exemplary coatings include chromophores like indocyanine green, vital blue, carbon black and methylene blue. The radiation, often ultraviolet or visible light must therefore be supplied in situ from a second device due to the poor penetration of the radiation through the tissue. Additionally, production of sufficient and uniform heat using this technique remains a challenge. Furthermore, the chromophores may degrade into unwanted chemicals that are toxic to the body. Therefore, there exists a need for an easier, less toxic and less invasive way to heat implants, including biodegradable polymer implants, to an elevated temperature so that they may be shaped or molded in situ. Furthermore, such techniques should also be able to heat the implant uniformly.

Additionally, while biodegradable implants will degrade over time, it would also be desirable to be able to control the rate of degradation. For example, when an implant is no longer required, it would be desirable to be able to accelerate the degradation rate so that the implant breaks down faster than its normal in situ rate. For this reason, there is also need for a way to control the degradation rate of a biodegradable implant.

2. Description of the Background Art

Prior patents describing nanoshells for converting incident radiation into heat include: U.S. Pat. Nos. 6,344,272; 6,428,811; 6,530,944; 6,645,517; 6,660,381; 6,685,730; 6,699,724; 6,778,316; and 6,852,252. Prior patents describing thermomechanically expansion of stents include: U.S. Pat. Nos. 5,670,161; 5,741,323; 6,607,553; 6,736,842. Prior patents describing meltable stents include: U.S. Pat. Nos. 4,690,684 and 4,770,176. Prior patent describing bioerodable polyanhydrides for controlled drug delivery include: U.S. Pat. No. 4,891,225. Prior patents describing tyrosine derived polycarbonate as an implant include: U.S. Pat. Nos. 6,951,053; 7,101,840; and 7,005,454. Prior patents describing biodegradable stents include: U.S. Pat. Nos. 5,733,327; 5,762,625; 5,817,100; 6,045,568; 6,080,177, 6,200,335; 6,413,272; 6,500,204; 6,632,242; RE38,653; RE38,711; U.S. Pat. Nos. 7,066,952;

and 7,070,615. The full disclosure of each of these patents is incorporated herein by reference.

BRIEF SUMMARY OF THE INVENTION

The invention generally provides for an implant having a plurality of particles dispersed therein. The particles are adapted to convert incident radiation into heat energy when the particles are irradiated with electromagnetic radiation. The particles are in thermal contact with the implant and therefore the heat generated by the particles raises the temperature of the implant. The increased temperature changes a material property of the implant.

In a first aspect of the present invention, an implant for use in tissue comprises a structure that is adapted for implantation into the tissue and that has a first material property at normal body temperature. The material property is variable at an elevated temperature above normal body temperature. The implant also comprises a plurality of particles that are dispersed in the structure and that are adapted to convert incident radiation into heat energy when the particles are irradiated with electromagnetic radiation. The particles are in thermal contact with the structure and thus exposure of the particles to incident radiation raises the temperature of the structure thereby changing the first material property.

In another aspect of the present invention, an expandable implant for use in tissue comprises a structure that is adapted for implantation into the tissue and that is not plastically deformable at normal body temperature but that is plastically deformable at an elevated temperature above normal body temperature. The implant also has a plurality of particles dispersed in the structure and that are adapted to convert incident radiation into heat energy when irradiated with electromagnetic radiation. The particles are in thermal contact with the structure such that exposure of the particles to the incident radiation raises the temperature of the structure allowing it to be plastically deformed.

In yet another aspect of the present invention, an expandable, biodegradable implant for use in tissue comprises a biodegradable structure that is adapted for implantation into the tissue and that degrades at a first rate when implanted in the tissue at normal body temperature. The implant also comprises a plurality of particles that are dispersed in the structure with the particles adapted to convert incident radiation into heat energy when they are irradiated with electromagnetic radiation. The particles are in thermal contact with the structure such that exposure of the particles to the incident radiation raises the temperature of the structure thereby increasing the degradation rate of the structure relative to the first rate.

The degradation rate of an implant may also be controlled by using an additional reagent such as a catalyst or enzyme. The reagent is adapted to react with the structure so as to increase the structure's degradation rate relative to the first rate at normal body temperature. Often, the reagent is dispersed in a carrier such as a microsphere along with particles such as nanoshells. The microsphere, which may be a hydrogel, is distributed in the implant structure and exposure of the particles to incident radiation raises the temperature of the carrier or microsphere, thereby releasing the reagent.

Often the structure is biodegradable and is composed of a polymer or copolymer, either synthetic or natural, that is not plastically expandable at normal body temperature but is thermo-mechanically expandable at an elevated temperature above normal body temperature. The structure is often composed of one or more of the following materials including, polyhydroxyalkanoates, polyalphahydroxy acids, polysaccharides, proteins, hydrogels, lignin, shellac, natural rubber, polyanhydrides, polyamide esters, polyvinyl esters, polyvinyl alcohols, polyalkylene esters, polyethylene oxide, polyvinylpyrrolidone, polyethylene maleic anhydride and poly (glycerol-sibacate). The structure may also comprise poly-L-lactide, poly-ε-caprolactone or a biological fluid in the solid state such as blood plasma. The material property may be the biodegradation rate of the structure, viscosity or the property may be the ability of the structure to be plastically expanded.

Sometimes the structure may be a stent which may be tubular and that is radially expandable at the elevated temperature. The stent may comprise a tube having a sidewall and the sidewall may define a plurality of openings therein. Sometimes the structure may also have a therapeutic agent that is adapted to be released therefrom. The therapeutic agent may be an anti-restenosis agent or it may be at least one of the following, including antibiotics, thrombolytics, anti-thrombotics, anti-inflammatories, cytotoxic agents, anti-proliferative agents, vasodilators, gene therapy agents, radioactive agents, immunosuppressants, chemotherapeutics, endothelial cell attractors, endothelial cell promoters, stem cells and combinations thereof. Sometimes the structure may be adapted to be implanted into a breast or it may be used to deliver a drug to the tissue. The structure may also be used to exclude aneurysms or it may be an orthopedic implant.

The particles may comprise nanoparticles or nanoshells and often the particles have a non-conducting core layer such as silicon dioxide, with a first thickness and a conducting outer shell layer, such as gold, adjacent to the core layer with a second thickness. The ratio of the first thickness to the second thickness defines a maximum wavelength of electromagnetic radiation converted by the particles into heat. Sometimes the particles are substantially spherical. Often the elevated temperature is in the range from about 38° C. to about 60° C. and the electromagnetic radiation often is ultraviolet, visible, near infrared or infrared light.

In another aspect of the present invention, a method of controlling a material property of an implant comprises the steps of providing an implant having a plurality of particles dispersed therein. The implant has a first material property when implanted in tissue at normal body temperature and the material property is variable at an elevated temperature above normal body temperature. Exposing the implant to electromagnetic radiation results in the incident radiation being converted into heat energy thus raising the temperature of the implant above normal body temperature and thereby changing the material property relative to the first material property.

In yet another aspect of the present invention, a method of delivering an expandable implant to a treatment site in a body comprises providing an implant having a plurality of particles dispersed therein and positioning the implant at the treatment site. Positioning may include advancing a catheter through a body lumen with the implant disposed on the catheter. Exposing the implant to electromagnetic radiation allows the particles to convert the incident radiation into heat energy. The heat energy raises the implant temperature above its glass transition temperature such that the implant may be plastically deformed so as to change its shape. Expanding the implant may include expanding a balloon.

In another aspect of the present invention, a method of controlling the degradation rate of an implant comprises providing a biodegradable implant having a plurality of particles dispersed therein. The implant degrades at a first rate when implanted in tissue at normal body temperature. Exposing the implant to electromagnetic radiation allows the particles to convert the incident radiation into heat energy which raises the temperature of the implant above normal body temperature. The elevated temperature changes the biodegradation rate of the implant relative to the first rate. Exposing the implant may include irradiating a carrier such as a microsphere, dispersed in the implant and containing a reagent and particles. The carrier heats up and releases the reagent when irradiated and the reagent reacts with the implant to degrade it. The reagent may be an enzyme or catalyst.

The method may also comprise discontinuing exposure of the implant to the electromagnetic radiation in order to allow the implant to cool down so that it returns to body temperature so that the implant is substantially undeformable plastically at body temperature. The method may also include monitoring the temperature of implant. Exposing the implant to electromagnetic radiation may include exposing the implant from outside the body or from within the body. Sometimes a catheter may be used to deliver the radiation to the implant. The radiation may be delivered for a fixed duration of time, continuously for a defined period or over periodic intervals until a desired temperature obtained in the implant.

These and other embodiments are described in further detail in the following description related to the appended drawing figures.

BRIEF DESCRIPTION OF THE DRAWINGS

FIGS. 5A-5E illustrate stent expansion in accordance with an exemplary embodiment.

FIGS. 6A-6E illustrate stent biodegradation in accordance with an exemplary embodiment.

FIGS. 8A-8D illustrate expansion of a breast implant in accordance with an exemplary embodiment.

DETAILED DESCRIPTION OF THE INVENTION

Figure 1A:
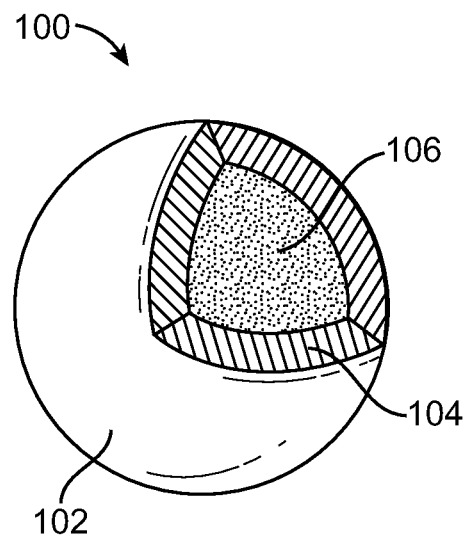
FIGS. 1A-1B show nanoshells having various outer shell thicknesses.
Figure 1B:
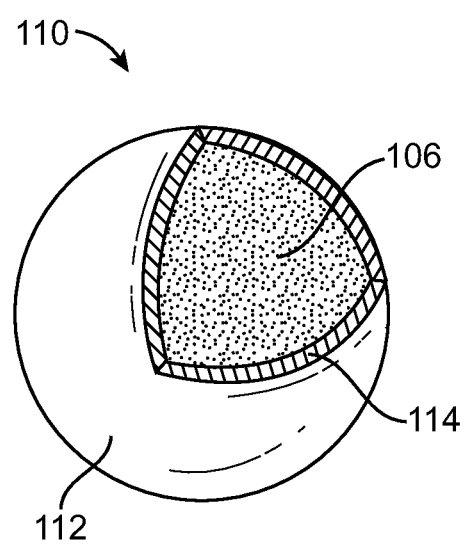

FIGS. 1A and 1B illustrate nanoshells having various outer shell thicknesses. Nanoshells are nanoparticles having a diameter ranging from a few nanometers up to about 5 microns. The nanoshells are composed of a non-conducting, semiconductor or dielectric inner core layer and an ultra thin conducting outer shell layer. In the exemplary embodiment of FIG. 1A, nanoshell 100 is spherically shaped and has an outer spherical shell 102 made from gold. A portion 104 of outer shell 102 has been removed in FIG. 1A so that the inner spherical core 106 is visible. Inner core 106 is made from silicon dioxide. Other common materials that may be utilized for the inner core include, but are not limited to, gold sulfide, titanium dioxide, polymethyl methacrylate, polystyrene and macromolecules such as dendrimers. Metals which are well suited for use in the outer shell also include, but are not limited to silver, copper, platinum, palladium, lead, iron and the like. Nanoshells may be made with various inner core diameters and outer shell thicknesses. FIG. 1B illustrates another nanoshell 110 having a thinner outer shell 112 compared with the outer shell 102 of FIG. 1A. The nanoshell in FIG. 1B also has a section 114 of outer shell 112 removed so that the inner core 106 is visible.

Nanoshells have a unique ability to interact with specific wavelengths of electromagnetic radiation and effectively convert the incident radiation into heat energy. By adjusting the relative core and shell thicknesses, and choice of materials, nanoshells can be fabricated that will react with or scatter light at any wavelength across much of the ultraviolet, visible and infrared range of the electromagnetic spectrum. The nanoshell may therefore be tuned to specific wavelengths of electromagnetic radiation and the conversion of incident radiation to heat energy can be optimized.

Figure 2:
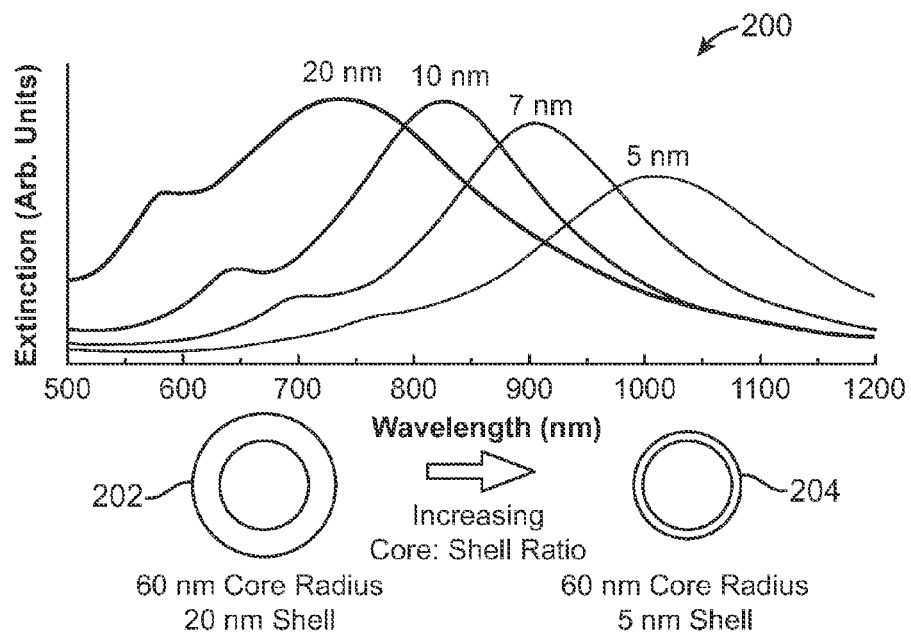
FIG. 2 illustrates the optical resonances of metal nanoshells having various ratios of core radius to shell thickness.

FIG. 2 shows a graph 200 of the optical resonances of metal nanoshells having various ratios of core radius to shell thickness. In FIG. 2, nanoshells 202 and 204 both have a 60 nm inner core made from silicon dioxide. Nanoshell 202 has a gold outer shell, 20 nm thick and the resulting maximum absorption wavelength is approximately 740 nm. As the shell thickness decreases, the maximum absorption wavelength increases. Nanoshell 204 has a gold shell layer 5 nm thick and the resulting maximum absorption wavelength is approximately 1010 nm. The tunability of nanoshells, including the relationship between the ratio of core diameter to shell thickness and maximum absorption wavelength is more fully discussed in U.S. Pat. No. 6,344,272 which has previously been incorporated herein by reference.

Nanoshells are well described in the scientific and patent literature. Other aspects of nanoshells such as manufacturing methods, materials and principles of operation are described in U.S. Pat. Nos. 6,428,811; 6,530,944; 6,645,517; 6,660,381; 6,685,730; 6,699,724; 6,778,316; and 6,852,252, the entire contents of which have previously been incorporated herein by reference.

Because nanoshells are efficient at converting incident radiation into heat, they may be dispersed in implants and light or other forms of electromagnetic radiation may be used to heat up the implant. Furthermore, since a nanoshell may be tuned to certain wavelengths, a nanoshell that preferentially interacts with light at near infrared wavelengths between approximately 700 and approximately 2500 nm is desirable, and more preferably between about 800 nm and 1200 nm, since this range of wavelengths is transmitted through tissue with very little absorption and therefore relatively little attenuation. Thus the majority of the light is delivered to the nanoparticles, converted into heat and transferred to the implant in which the nanoparticles are dispersed. This makes external access to an implanted device possible and heating of the tissue surrounding the implant is substantially avoided. One particular source of near infrared light, a Nd:YAG laser emits light at a wavelength of 1064 nm and hence is ideal for irradiating an implant from outside the body. Additionally, in the case of a biodegradable implant, as the implant breaks down the nanoshells are released into surrounding tissue. Due to their small size, the nanoshells are easily purged by body systems such as the kidneys. Nanoshells therefore present a unique way of allowing an implant to be heated from outside the body with minimal biocompatibility issues.

Figure 3A:
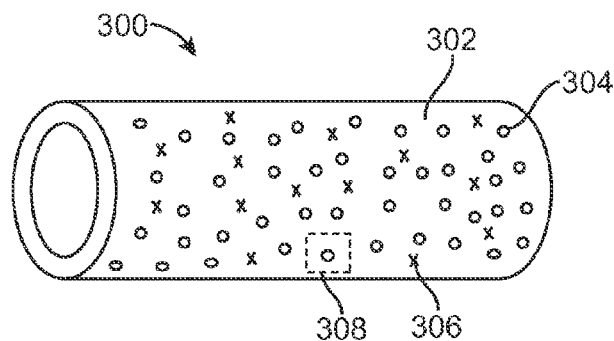
FIG. 3A shows a biodegradable stent having nanoshells dispersed therein.

FIG. 3A shows an implantable stent 300. Stents are defined to include any of the array of expandable prostheses and scaffolds which are introduced into a lumen at a target treatment site and expanded in situ thereby exerting a radially outward force against the lumen wall to restore patency. Stents may be implanted in a number of lumens including the coronary and peripheral vasculature, biliary ducts, urethra and ureter, as well as other body cavities. Urethral and ureter stents are well reported in the patent literature, including for example U.S. Pat. Nos. 7,112,226 and 7,044,981, the entire contents of which are incorporated herein by reference. Other stents are discussed and incorporated below. Stent 300 is a tubular prosthesis made from any material 302 that is solid at normal body temperature and that may be plastically deformed at an elevated temperature. Examples include standard engineering thermoplastics such as polyurethane and others well known to those skilled in the art, including biodegradable polymers like polylactide. Stent 300 may optionally be a copolymer containing 2-10% of poly-$\epsilon$-caprolactone so as to adjust the mechanical properties of the stent, including lowering the glass transition temperature to just above normal body temperature. In preferred embodiments, the copolymer stent 300 has a glass transition temperature in the range from about 40° to about 60° C. Stent 300 may also comprise plasticizers to further soften the implant. The plasticizers should be biocompatible such as oleic acid and linoleic acid which are classified under Food and Drug Administration (FDA) guidelines for food additives as being Generally Recognized as Safe (GRAS). The stent 300 may be delivered to the site of a stenotic lesion or an intimal dissection and expanded in situ in order to restore patency of a vessel.

In FIG. 3A, preferably 0.0001 to 1% nanoparticles 304, more preferably 0.00025% to 0.5%, and most preferably 0.0005% to 0.1% nanoparticles are dispersed in the stent 300. The nanoparticles 304 may be tuned to interact with many forms of electromagnetic radiation including microwaves, ultrasound, magnetic fields, electric fields, radiofrequency, infrared, visible, ultraviolet, laser, x-rays, gamma rays and cosmic rays. However, in this exemplary embodiment, the nanoparticles 304 are preferably tuned to interact with near infrared radiation having a wavelength approximately 1064 nm so that that a Nd:YAG laser may be used to irradiate stent 300 from outside the body. The nanoparticles 304 in this embodiment are preferably nanoshells having an outer shell composed of gold and an inner core composed of silicon dioxide. The nanoparticles 304 convert the incident radiation into heat, thereby heating the polymer matrix above its glass transition temperature and allowing stent 300 to be plastically deformed into a lesion with a balloon or other expandable member in situ. Optionally, stent 300 may also include quantum dots dispersed therein. Quantum dots have many desirable characteristics, including favorable optical properties. The quantum dots may be used to help visualize stent 300 while in situ since they fluoresce when irradiated with certain wavelengths of light. Examples of materials used to fabricate quantum dots include cadmium selenide, cadmium sulfide, zinc sulfide and zinc selenide.

Figure 3B:
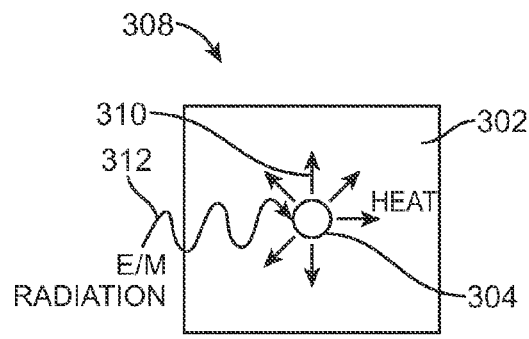
FIG. 3B shows a nanoshell generating heat in a section of the stent shown in FIG. 3A.

FIG. 3B illustrates a section 308 of FIG. 3A which has been enlarged to show how incident radiation 312 interacts with nanoparticle 304 such that the radiation 312 is converted into heat by nanoparticle 304 and the heat 310 is emitted to the surrounding polymer matrix 302. In this exemplary embodiment, stent 300 is a tubular prosthesis without any apertures in the sidewalls and therefore it could also be used to exclude an aneurysm. However, this is not meant to be limiting and stent 300 may be modified to include apertures in the sidewalls.

In many of the embodiments described herein, near infrared light is used to irradiate the nanoparticles and generate heat. However, it should be obvious to one of ordinary skill in the art that many wavelengths of electromagnetic radiation may also be used, including a magnetic field. The nanoparticles may be magnetically responsive so that they produce heat upon exposure to a magnetic field. Examples of magnetically responsive materials include iron oxides, magnetite ($Fe_3O_4$) and maghemite ($\gamma$-$Fe_2O_3$).

Figure 4A:
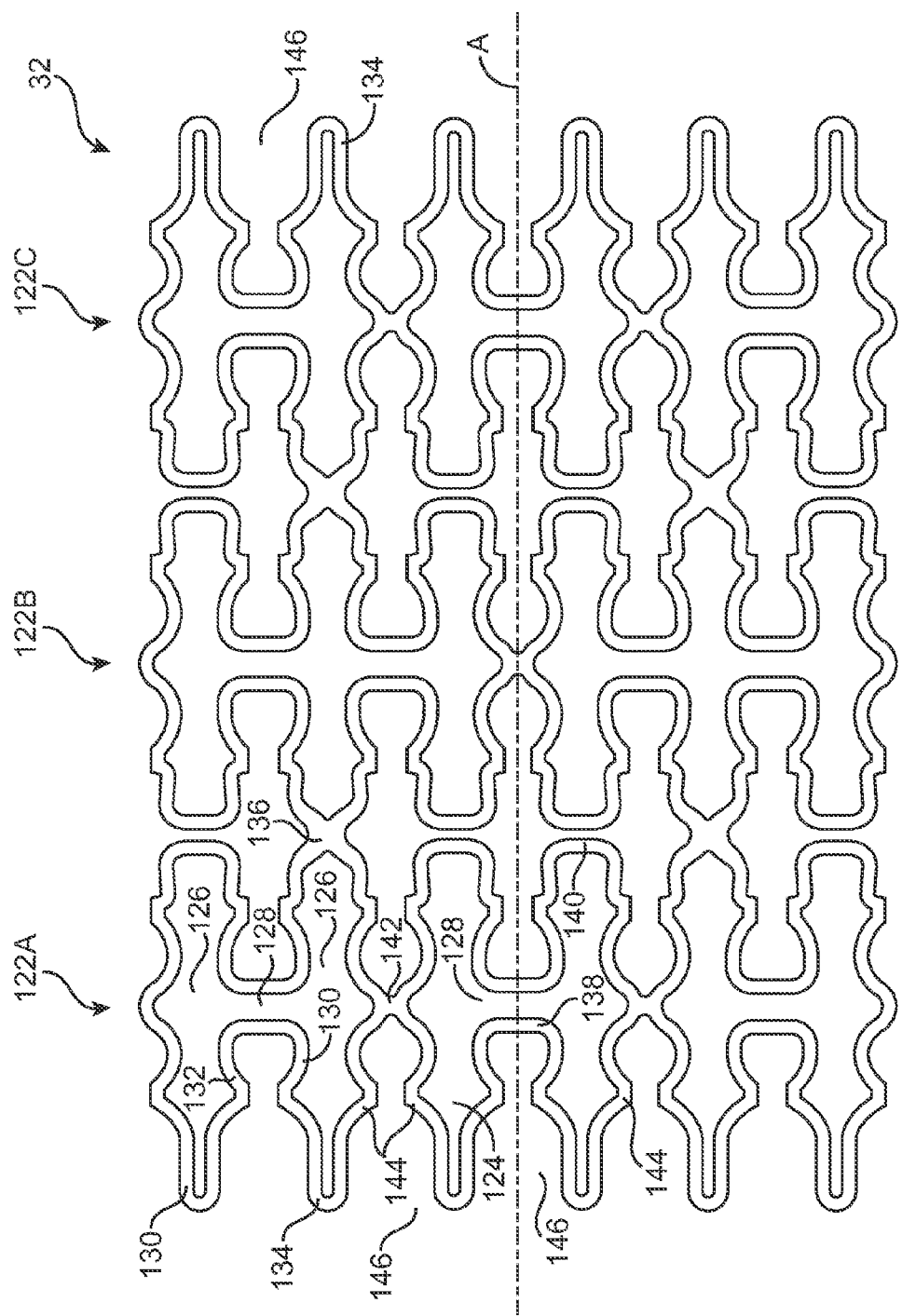
FIGS. 4A-4B illustrate a preferred embodiment of a stent in the unexpanded and expanded state.
Figure 4B:
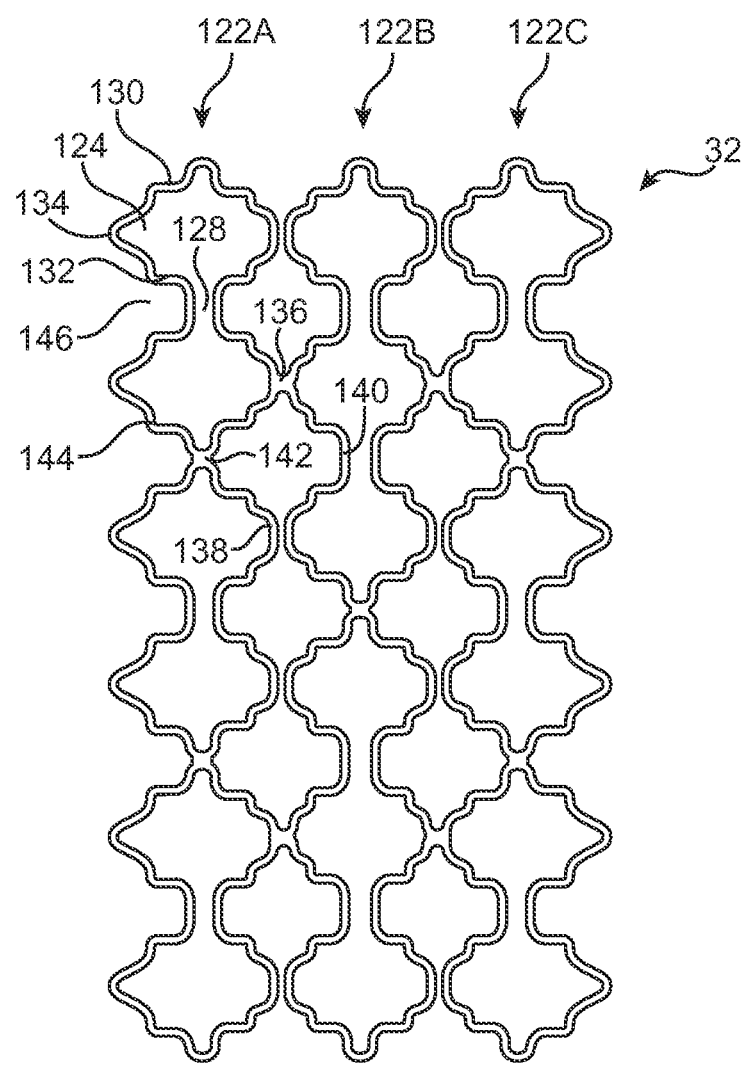

FIGS. 4A and 4B illustrate a preferred embodiment of one possible stent geometry. In FIG. 4A a portion of stent segment 32 is shown in a planar shape for clarity. Stent segment 32 comprises parallel rows 122A, 122B and 122C of I-shaped cells 124 formed into a cylindrical shape around axial axis A. Cells 124 have upper and lower axial slots 126 and a connecting circumferential slot 128. Upper and lower slots 126 are bounded by upper axial struts 132, lower axial struts 130, curved outer ends 134, and curved inner ends 136. Circumferential slots 128 are bounded by outer circumferential strut 138 and inner circumferential strut 140. Each I-shaped cell 124 is connected to the adjacent I-shaped cell 124 in the same row 122 by a circumferential connecting strut 142. Row 122A is connected to row 122B by the merger or joining of curved inner ends 136 of at least one of upper and lower slots 126 in each cell 124.

In FIGS. 4A-4B, the stent includes a bulge 144 in upper and lower axial struts 130, 132 extending circumferentially outwardly from axial slots 126. These give axial slots 126 an arrowhead or cross shape at their inner and outer ends. The bulge 144 in each upper axial strut 130 extends toward the bulge 144 in a lower axial strut 132 in the same cell 124 or in an adjacent cell 124, thus creating a concave abutment 146 in the space between each axial slot 126. Concave abutments 146 are configured to receive and engage curved outer ends 134 of cells 124 in the adjacent stent segment, thereby maintaining spacing between the stent segments. The axial location of bulges 144 along upper and lower axial struts 130, 132 may be selected to provide the desired degree of inter-segment spacing.

FIG. 4B shows a stent 32 of FIG. 4A in an expanded condition. It may be seen that axial slots 124 are deformed into a circumferentially widened modified diamond shape with bulges 144 on the now diagonal upper and lower axial struts 130, 132. Circumferential slots 128 are generally the same size and shape as in the unexpanded configuration. Bulges 144 have been pulled away from each other to some extent, but still provide a concave abutment 146 to maintain a minimum degree of spacing between adjacent stent segments. As in the earlier embodiment, some axial shortening of each segment occurs upon expansion and stent geometry can be optimized to provide the ideal intersegment spacing.

It should also be noted that the embodiment of FIGS. 4A-4B also enables access to vessel side branches blocked by stent segment 32. Should such side branch access be desired, a dilatation catheter may be inserted into circumferential slot 128 and expanded to provide an enlarged opening through which a side branch may be entered.

A number of other stent geometries are applicable and have been reported in the scientific and patent literature. Other stent geometries include, but are not limited to those disclosed in the following U.S. Patents, the full disclosures of which are incorporated herein by reference: U.S. Pat. Nos. 6,315,794; 5,980,552; 5,836,964; 5,527,354; 5,421,955; 4,886,062; and 4,776,337.

Referring back to FIG. 3A, stent 300 may also comprise a therapeutic agent 306. In preferred embodiments, stent 300 may be coated, impregnated, infused or otherwise coupled with one or more drugs that inhibit restenosis, such as Rapamycin, Everolimus, Biolimus A9, Paclitaxel, prodrugs, or derivatives of the aforementioned, or other suitable agents, preferably carried in a durable or bioerodable carrier of polymeric or other suitable material. Alternatively, stent 300 may be coated with other types of drugs or therapeutic materials such as antibiotics, thrombolytics, anti-thrombotics, anti-inflammatories, cytotoxic agents, anti-proliferative agents, vasodilators, gene therapy agents, radioactive agents, immunosuppressants, chemotherapeutics, endothelial cell attractors or promoters and/or stem cells. Such materials may be coated over all or a portion of the surface of stent 300, or stent 300 may have a porous structure or include apertures, holes, channels, or other features in which such materials may be deposited.

Figure 3C:
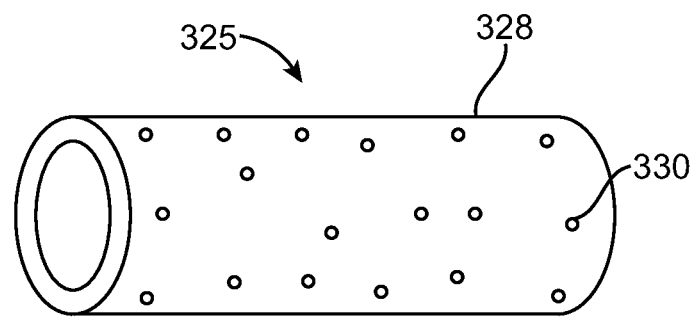
FIG. 3C shows an implant made from frozen biological fluid and having nanoshells dispersed therein.
Figure 3D:
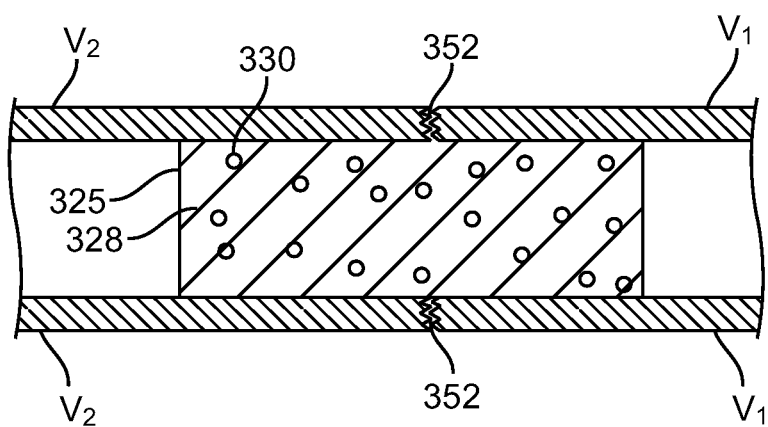
FIG. 3D shows the implant of FIG. 3C used to facilitate creation of an anastomosis.

FIG. 3C illustrates an implant where nanoshells may be used to control the degradation of the implant. In an exemplary embodiment, a stent 325 is adapted for creating an anastomosis. The stent 325 may be made from a variety of meltable materials including polymers, frozen blood plasma or other biological fluids in the solid state. Nanoshells 330 are dispersed in the stent 325. FIG. 3D shows the stent 325 placed into the ends V1, V2 of the two vessels to be connected together, thereby aligning the ends together so that they may be sutured or thermally bonded together, creating an anastomosis 352. In this embodiment, after the stent 325 has been placed into the vessel ends, V1, V2, and the ends have been connected together, stent 325 may be irradiated with near infrared light from outside the body. The nanoshells 330 convert the incident radiation into heat. The resulting heat melts the stent 325 thereby creating a patent lumen for fluid flow. Further details on meltable stents are disclosed in U.S. Pat. Nos. 4,690,684 and 4,770,176, the entire contents of which are fully incorporated herein by reference.

Figure 5A:
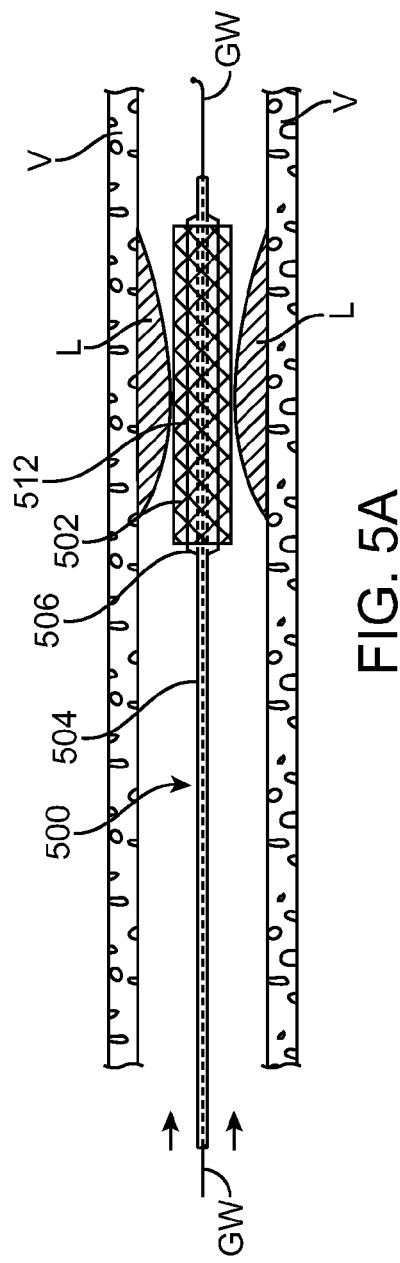

Referring now to FIGS. 5A-5E, the deployment of a stent to treat a stenotic lesion is shown in accordance with an exemplary embodiment. While the embodiment will be described in the context of a femoral artery stent procedure, it should be understood that the invention may be employed in any variety of coronary or peripheral arteries, blood vessels and other body lumens in which stents or tubular prostheses are deployed, including the carotid and iliac arteries, blood vessels in the brain, other arteries or veins, as well as non-vascular body lumens such as the ureter, urethra, fallopian tubes, the hepatic and biliary duct and the like. In FIG. 5A, a stent delivery catheter 500 includes a stent 502 having a plurality of nanoshells 512 dispersed therein and mounted over an expandable balloon 506 attached to the distal end of catheter shaft 504. In this exemplary embodiment, a single biodegradable stent 502 is disposed on the delivery catheter 500, although multiple stents may also be disposed on the delivery catheter 500. Stent 502 is preferably composed of a copolymer containing approximately 90 to 99% polylactide with 1 to 10% poly-ε-caprolactone, and more preferably 95 to 99% polylactide with 1 to 5% poly-ε-caprolactone, uniformly blended with preferably 0.0001 to 1% gold nanoshells, more preferably 0.00025% to 0.5%, and most preferably 0.0005% to 0.1% gold nanoshells that are tuned to convert near infrared light into heat. Stent 502 may also be fabricated from any material that is solid at normal body temperature and that can be plastically deformed at an elevated temperature, thus many other polymers such as polyurethanes as well as other biodegradable materials may be used to fabricate the stent 502. Delivery catheters such as over-the-wire systems and rapid exchange systems are well known in the art and may be used to deliver stent 502 to the lesion L.

Having multiple stents allows the physician operator to select the number of stents to deliver and thus customization of stent length is possible, as disclosed in U.S. Patent Publication Nos. 2006/0282150 and 2007/0027521, the entire contents of which are incorporated herein by reference. Additionally, other customizable-length stent delivery systems have been proposed for delivering multiple stent segments and these may also be used to deliver one or more stents 502. Prior publications describing catheters for delivering multiple segmented stents include: U.S. Pat. Nos. 7,309,350; 7,326,236; 7,137,993; and 7,182,779; U.S. Patent Publication Nos. 2005/0038505; 2004/0186551; and 2003/0135266. Prior related U.S. Patent Applications, Publications and Provisionals include serial Nos. 2006/0282150; 2006/0282147; 2007/0179587; 2007/0067012; 60/784,309; and 11/462,951. The full disclosures of each of these patents and applications are incorporated herein by reference.

In FIG. 5A, the delivery catheter 500 is introduced into a treatment vessel first, by placing an introducer sheath (not illustrated) into the target peripheral artery, typically using a percutaneous procedure such as the Seldinger technique or by surgical cutdown. In this exemplary embodiment, the target vessel is a femoral artery. The introducer sheath is then advanced slightly into the femoral artery. A guidewire GW is then inserted through the introducer and advanced into the target vessel V where a lesion L to be treated is located. The proximal end of guidewire GW is then inserted through the distal end of catheter shaft 504, through a lumen in catheter shaft 504, exiting at the proximal end of catheter shaft 504, which is outside the patient's body.

Stent delivery catheter 500 is then slidably advanced over the guidewire GW into the vessel V so that stent 502 traverses the lesion L. Optional radiopaque markers (not illustrated) may be placed on the catheter shaft 504 in order to facilitate visualization of the delivery catheter under fluoroscopy. Once the delivery catheter has been properly positioned in the vessel, the stent 502 may be heated up to facilitate its expansion.

Figure 5B:
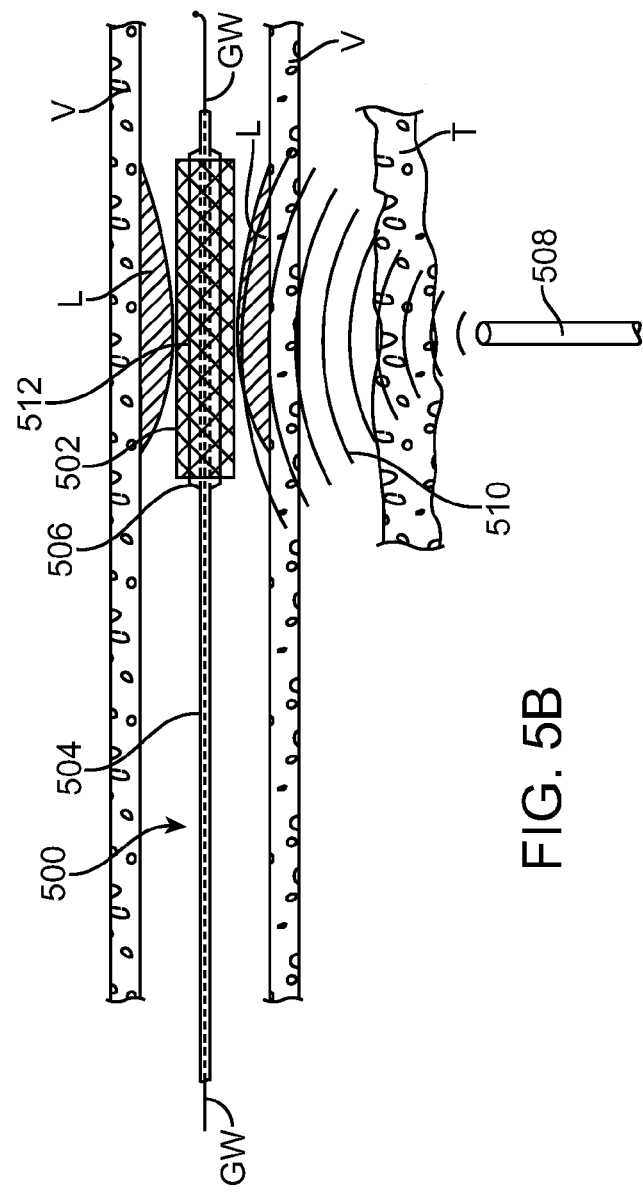

In FIG. 5B, an external source of electromagnetic radiation 508 is used to irradiate stent 502 so as to heat it up. In FIG. 5B, the external source of radiation is preferably a Nd:YAG laser which emits a wavelength of light approximately 1064 nm. This wavelength is applied extracorporally and the light 510 is transmitted through the tissue T to the stent 502. Nanoshells 512 dispersed in the stent 502 are tuned to convert the light into heat. Heat generated by nanoshells 512 is transferred to the polymer which makes up stent 502, thereby heating it up. In addition or as an alternative to applying extracorporeal radiation, radiation may be applied in situ. FIG. 5C shows a fiber optic catheter 514 deployed alongside delivery catheter 500. The fiber optic catheter 514 is adapted to deliver the Nd:YAG laser light 516 directly to stent 502. In some embodiments, the delivery catheter 500 and the fiber optic catheter 514 may be combined into a single device that heats and deploys stent 502. In some embodiments, fiber optic catheter 514 includes an optional diffuser (not shown). The diffuser is adapted to spread out and scatter the radiation so as to cover a larger area of the stent 502.

Radiation is applied until the temperature of stent 502 is above its glass transition temperature, $T_g$, which is approximately 40°-60° C. in this exemplary embodiment. The exposure time is dependent upon many factors, including but not limited to, area of radiation coverage, wavelength and intensity of the radiation, type and mass of the implant material and nanoshell concentration. Therefore, exposure time could range from a few seconds to a few hours, and more preferably from about 10 seconds to about an hour. Longer exposure times are not desirable due to patient inconvenience.

Stent 502 is fabricated from a material having a glass transition temperature above normal body temperature. Therefore, stent 502 is solid at or below normal body temperature. Normal body temperature is approximately 37° C., therefore the stent 502 material is selected to have a $T_g$ slightly higher than 37° C., yet not so high that the temperature required to heat the stent above $T_g$ results in tissue damage.

Figure 5E:
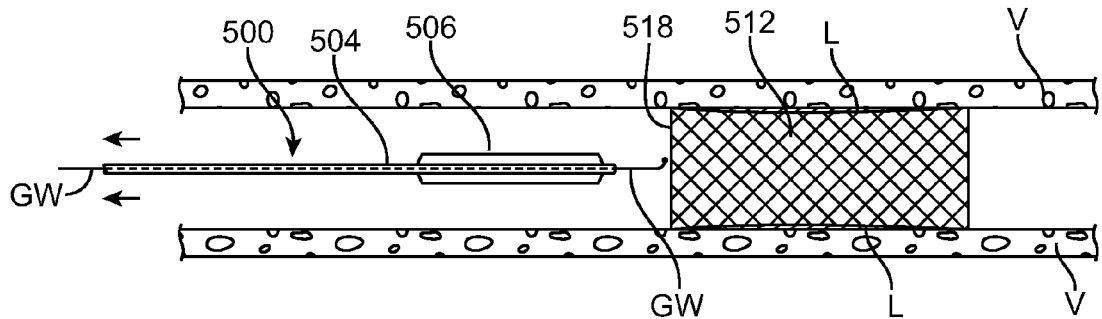

Once the temperature of stent 502 is raised above the glass transition temperature, it's viscosity decreases, permitting stent 502 to be plastically deformed. In FIG. 5D, balloon 506 is expanded, typically with contrast media and/or saline and an inflation device such an Indeflator™, manufactured by Abbott (formerly Guidant Corp., Santa Clara, Calif.). Stent 502 is soft and therefore expands with balloon 506 to an expanded state 518, covering lesion L. After stent 502 has been enlarged to its expanded state 518, application of radiation may be discontinued, allowing stent 518 to cool down to body temperature. When stent 518 cools down, it solidifies and permanently retains its expanded shape. In FIG. 5E, balloon 506 is then deflated and delivery catheter 500 is withdrawn from the vessel, leaving stent 518 with nanoshells 512 in place. Stent 518 is composed of biodegradable materials and therefore, over time will degrade, releasing nanoshells 512 into the vascular system where they will be filtered and purged out of the body by the kidneys.

Figure 8A:
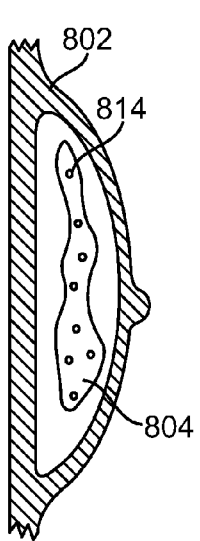

Referring now to FIGS. 8A-8D, the expansion of an implant for breast augmentation during cosmetic and reconstructive procedures (e.g. after mastectomy) is shown in accordance with an exemplary embodiment. In FIG. 8A, an implant 804 having nanoparticles 814 dispersed therein is implanted using standard surgical or minimally invasive techniques into a breast 802. The implant may be any biocompatible thermoplastic or material that is solid at normal body temperature and that may be plastically deformed upon heating. Examples of such materials include, but are not limited to polyurethanes, polyethylene, and PVC. Nanoparticles 814 may be tuned to convert any wavelength of electromagnetic radiation into heat, however, in this exemplary embodiment, nanoparticles 814 are tuned to near infrared light, such as that provided by a Nd:YAG laser.

Figure 8B:
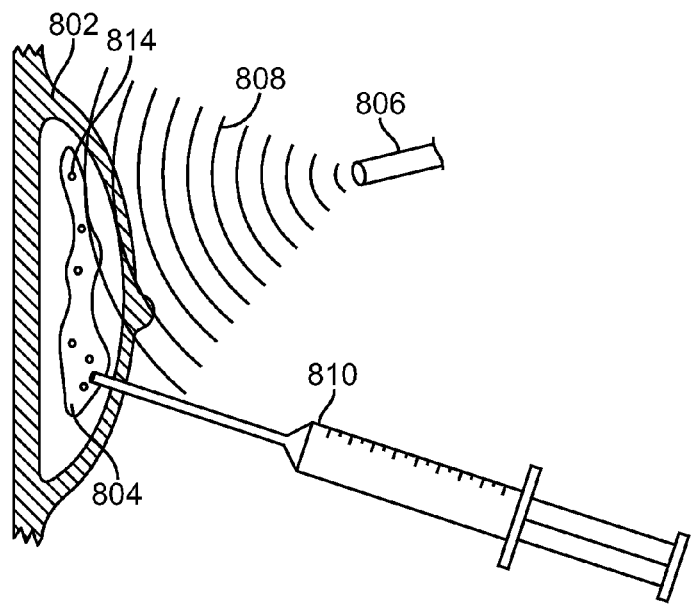

In FIG. 8B, the breast 802 is irradiated with near infrared light 808 from an Nd:YAG laser 806. As previously discussed, this wavelength of light is easily transmitted through tissue without being attenuated. The light 808 therefore irradiates the nanoparticles 814, here preferably nanoshells having a gold outer shell and a silicon dioxide inner core, such that the incident radiation is converted into heat. The heat raises the temperature of implant 802 above its glass transition temperature, lowering its viscosity and softening the implant 802. A syringe 810 may then be used to fill the implant 804 with a fluid such as saline in order to expand the implant to a larger volume as seen in FIG. 8C. Once the breast 802 has been enlarged to a desired size and/or shape, irradiation 808 may be suspended allowing the implant 804 to cool down and solidify and permanently retain the expanded shape. Syringe 810 may then be removed as shown in FIG. 8D. In alternative embodiments, other expandable members, such as a balloon catheter could be used to expand the implant. Additionally, repeat treatments may be applied as required in order to fine tune the implant to obtain a more desirable clinical result, or to accommodate changes in breast size or shape that occur with aging. Similar implants may also be used in other areas of the body, such as for shaping the chin, nose, lips, face, buttocks, calf, legs, thighs, legs, or any part of the body.

Figure 6A:
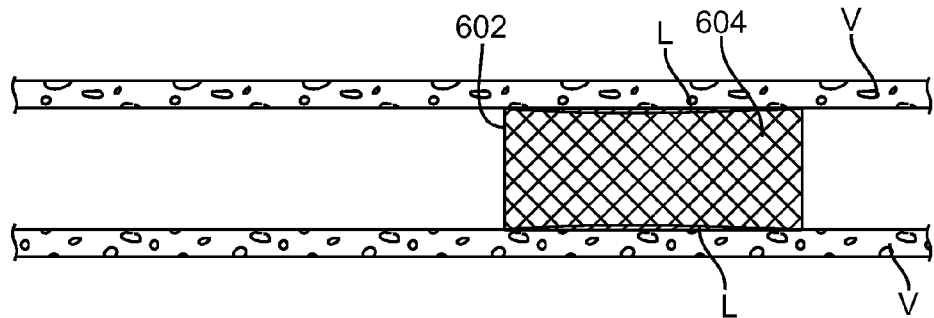

Nanoshells may also be used to control the degradation rate of a biodegradable implant. FIGS. 6A-6E illustrate a method of controlling the degradation rate of a biodegradable implant by using nanoshells to heat up the implant, thereby accelerating the rate at which the implant degrades in situ. In this exemplary embodiment, degradation of a stent is described. However, this is not meant to be limiting, as biodegradation of a number of other implants may be controlled in a similar manner. For example, ureteral implants, ocular implants or drug delivery devices (e.g. for treatment of cancer or diabetes), need only be implanted for a limited time, therefore it is desirable to be able to accelerate their degradation so as to avoid having to surgically remove them. In FIG. 6A, a stent 602 has been expanded and implanted at the site of a stenotic lesion L in a vessel V. The vessel may be a coronary artery, a peripheral artery or any body lumen or cavity. Stent 602 is composed of a biodegradable polymer having a plurality of nanoshells 604 dispersed therein. In this exemplary embodiment, stent 602 is preferably composed of a copolymer having approximately 90 to 99% polylactide and 1 to 10% poly-ϵ-caprolactone, and more preferably 95 to 99% polylactide and 1 to 5% poly-ϵ-caprolactone, uniformly blended with 0.0001 to 1%, more preferably 0.00025% to 0.5% and most preferably 0.0005% to 0.1% gold nanoshells that are tuned to convert near infrared light having a wavelength in the range from about 700 nm to about 2500 nm, and more preferably between about 800 nm and 1200 nm into heat. Other biodegradable polymers and nanoshells are possible, and this exemplary embodiment is not intended to be limiting.

Some examples of other biodegradable materials include polyesters such as polyhydroxyalkanoates (PHA) and poly-alphahydroxy acids (AHA). Exemplary PHAs include, but are not limited to polymers of 3-hydroxypropionate, 3-hydroxybutyrate, 3-hydroxyvalerate, 3-hydroxycaproate, 3-hydroxyheptanoate, 3-hydroxyoctanoate, 3-hydroxynonanoate, 3-hydroxydecanoate, 3-hydroxyundecanoate, 3-hydroxydodecanoate, 4-hydroxybutyrate and 5-hydroxyvalerate. Examples of AHAs include, but are not limited to various forms of polylactide or polylactic acid including PLA, PLLA or PDLLA, polyglycolic acid and polyglycolide, poly(lactic-co-glycolic acid), poly(lactide-co-glycolide), poly(ϵ-caprolactone) and polydioxanone. Polysaccharides including starch, glycogen, cellulose and chitin may also be used as a biodegradable material. It is also feasible that proteins such as zein, resilin, collagen, gelatin, casein, silk or wool could be used as a biodegradable implant material. Still other materials such as hydrogels including poly(hydroxyethyl methylacrylate), polyethylene glycol, poly(N-isopropylacrylamide), poly(N-vinyl-2-pyrrolidone), cellulose polyvinyl alcohol, silicone hydrogels, polyacrylamides, and polyacrylic acid are potential biodegradable implant materials. Other potential biodegradable materials include lignin, shellac, natural rubber, polyanhydrides, polyamide esters, polyvinyl esters, polyvinyl alcohol, polyalkylene esters, polyethylene oxide, polyvinylpyrrolidone, polyethylene maleic anhydride and poly(glycerol-sibacate). Still another potential biodegradable material include the polyphosphazenes developed by Harry R. Allcock at Pennsylvania State University.

Figure 6B:
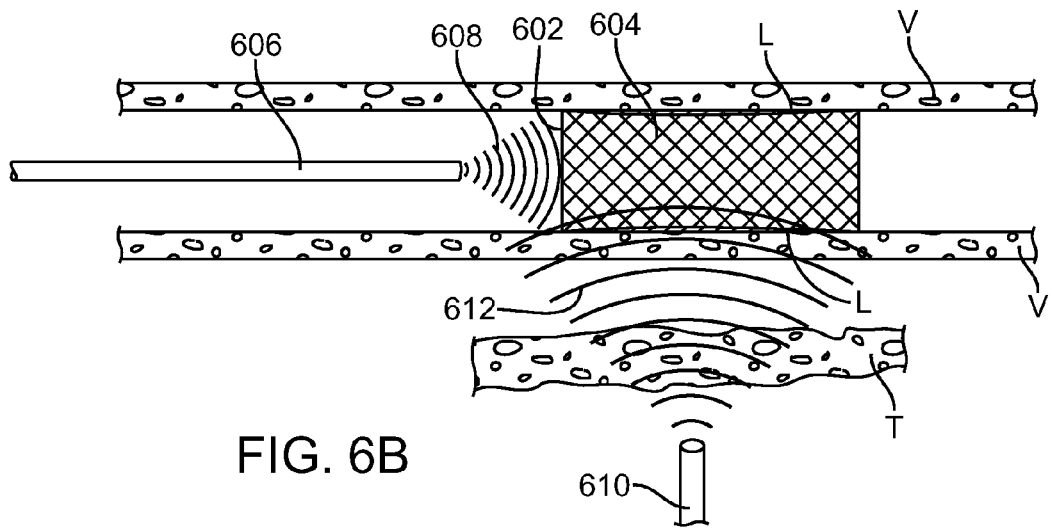

In FIG. 6B, a Nd:YAG laser 610 is used to extracorporally irradiate stent 602 with near infrared light 612. Light 612 supplied from laser 610 is at a wavelength approximately 1064 nm which can pass through tissues T without being significantly absorbed. The light 612 irradiates stent 602 and nanoshells 604 dispersed in the stent 602 interact with the light 612 and convert it into heat which raises the temperature of stent 602. Optionally, as an alternative or supplement to light 612 from laser 610, a fiber optic catheter 606 may be advanced to the site of the stent 602 using standard catheter delivery techniques and near infrared light 608 from a Nd:YAG laser may be intravascularly delivered to stent 602 to further irradiate stent 602. The exposure time is dependent upon many factors, including but not limited to, area of radiation coverage, wavelength and intensity of the radiation, type and mass of biodegradable material, nanoshell concentration, and concentration of any catalysts or enzymes in the implant. Therefore, exposure time could range from a few seconds to a few hours, and more preferably from about 10 seconds to about an hour. Exposure times greater than an hour, such as those seen in phototherapy regimes used to treat neonatal jaundice or in Crigler-Najjar syndrome (e.g. 12 hours/day) become impractical due to patient inconvenience. Stent 602 is irradiated to a temperature above the glass transition temperature, which as described above is selected to be slightly higher than normal body temperature and low enough to minimize potential tissue thermal damage.

As stent 602 temperature increases, naturally occurring chemical reactions between the body and the stent 602 are accelerated, thereby increasing the rate at which stent 602 breaks down. In FIG. 6C, stent 602 has partially degraded. Continued irradiation of stent 602 with near infrared light 608 and 612 maintains the stent 602 at an elevated temperature and the stent continues to break down as shown in FIG. 6D. This process continues until the entire stent 602 has degraded into low molecular weight, non-toxic products and therefore is removed from lesion L, as shown in FIG. 6E. Nanoshells 604 in the stent 602 are released into the vascular system during degradation and they are small enough to be filtered out of the body by the kidneys.

Figure 7:
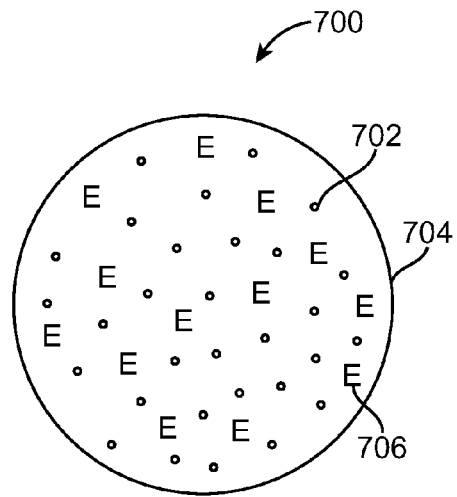
FIG. 7 illustrates a microsphere containing nanoshells and a chemical reagent dispersed therein.

In alternative embodiments, a microsphere containing nanoshells and a chemical reagent may be dispersed in the implant and used to accelerate biodegradation even more than previously described. FIG. 7 illustrates a microsphere 700, having a diameter approximately in the range of 1-10 μm and made from a hydrogel 704 such as polyvinyl alcohol, sodium polyacrylate, acrylate polymers and copolymers having an abundance of hydrophilic groups. Other hydrogels have been previously discussed. Nanoshells 702 are dispersed within the microsphere 700 along with a chemical reagent 706. The reagent may be any substance which reacts with an implant to degrade it. Examples of possible reagents include, but are not limited to hydrolases that catalyze hyrolysis of various bonds, lyases that cleave various bonds by means other than hydrolysis or oxidation and oxidases that cause oxidation. The use of these reagents can accelerate the rate of biodegradation relative to the method described above with respect to FIGS. 6A-6E. When the microsphere 700 is irradiated, the nanoshells 702 convert the incident radiation into heat thereby raising the temperature of microsphere 700. As described previously, the irradiation time is dependent upon many factors, including but not limited to, area of radiation coverage, intensity of the radiation, type and mass of biodegradable polymer, nanoshell concentration, hydrogel water concentration, and concentration of any catalysts or enzymes in the implant. Therefore, exposure time could range from a few seconds to a few hours, and more preferably from about 10 seconds to about an hour. In some embodiments, it may be desirable to spread the implant irradiation over multiple sessions, such a weekly, monthly or daily either for patient convenience or to control the bioerosion process.

As the microsphere 700 is irradiated and heats up, it expands and releases the reagent E into the implant material. The reagent begins to chemically react with the implant material, breaking it down, thus accelerating the in situ biodegradation rate. Additional information on methods of use, materials and principles of operation of controlled drug delivery systems are reported in the scientific and patent literature including U.S. Pat. Nos. 6,645,517 (West et al.) and U.S. Pat. No. 4,891,225 (Langer et al.), the entire contents of which are incorporated herein by reference. In other embodiments, an implant having different layers of degradable materials could be independently degraded by selectively releasing various reagents E from the microsphere 700 at different temperatures. The various layers could be bioeroded away at the same time during a single treatment session, or the layers may be selectively bioeroded away with multiple exposures to electromagnetic radiation at different times.

While the exemplary embodiments have been described in some details for clarity of understanding and by way of example, a variety of additional modifications, adaptations and changes may be clear to those of skill in the art. Hence, the scope of the present invention is limited solely by the appended claims.

What is claimed is:

1. A method of controlling a material property of a stent, the method comprising:
    providing a polymeric stent having a plurality of metallic nanoshells dispersed therein, wherein the nanoshells are covered with a metal selected from the group consisting of palladium, silver, platinum, and gold, and wherein the stent has a first material property when implanted in tissue at normal body temperature, the material property being variable at an elevated temperature above normal body temperature; and
    exposing the stent to electromagnetic radiation in the range of about 800 nm to 1200 nm, the incident radiation being converted into heat energy via the plurality of nanoshells thus uniformly raising the temperature of the stent above normal body temperature, thereby changing the material property relative to the first material property wherein the material property is either:
    (i) the ability of the stent to be plastically deformed such that the stent is not plastically deformable at normal body temperatures but is plastically deformable at an elevated temperature above normal body temperature or
    (ii) the viscosity of the stent where the stent has a lower viscosity at an elevated temperature above normal body temperature.

2. The method of claim 1, wherein the stent temperature is raised to a temperature In the range from about 38° C. to about 60° C.

3. The method of claim 1, wherein exposing the stent to electromagnetic radiation comprises delivering electromagnetic radiation to the stent with a catheter.

4. The method of claim 1, wherein exposing the stent to electromagnetic radiation comprises delivering the radiation until a desired temperature is obtained in the implant.

5. The method of claim 1, wherein the stent is biodegradable.

6. The method of claim 1, further comprising releasing a therapeutic agent from the stent in a controlled manner.

7. The method of claim 1, wherein the metallic nanoshells are covered with gold.

8. The method of claim 1, further comprising generating the electromagnetic radiation with a laser light source.

* * * * *